United States Patent [19]
Alexander

[11] Patent Number: 5,553,791
[45] Date of Patent: Sep. 10, 1996

[54] FORMING FINE PARTICLES

[75] Inventor: Dennis R. Alexander, Lincoln, Nebr.

[73] Assignee: The Board of Regents of the University of Nebraska, Lincoln, Nebr.

[21] Appl. No.: 391,058

[22] Filed: Feb. 21, 1995

Related U.S. Application Data

[60] Division of Ser. No. 371, Jan. 4, 1993, Pat. No. 5,390,864, and a continuation-in-part of Ser. No. 712,724, Jun. 10, 1991, Pat. No. 5,176,328, which is a division of Ser. No. 492,928, Mar. 13, 1990, Pat. No. 5,044,565.

[51] Int. Cl.$^6$ .................................................. B02C 19/00
[52] U.S. Cl. ............................ 241/1; 241/18; 241/38
[58] Field of Search .................................. 241/1, 18, 38, 241/39, 41, 301; 606/2.5

[56] References Cited

U.S. PATENT DOCUMENTS 4,020,317  4/1977  Colgate .............................. 241/1 X

FOREIGN PATENT DOCUMENTS 2351675  4/1975  Germany ................................ 241/1
1382492  3/1988  U.S.S.R. ................................ 241/1

Primary Examiner—Timothy V. Eley
Attorney, Agent, or Firm—Vincent L. Carney

[57] ABSTRACT

To alter feedstock material, the material is exposed to laser radiation applied at a selected angle of incidence, intensity and wavelength related to the refractive index of the feedstock material. Fine uniform particles may be formed through vapor explosion and/or plasma formation and used by this method to coat surfaces, such as with paint or adhesive or to supply uniform small particles to a heat engine. Moreover, moving materials such as a column of liquid may be subjected to high internal pressure and temperature for creating physical and chemical changes.

19 Claims, 8 Drawing Sheets

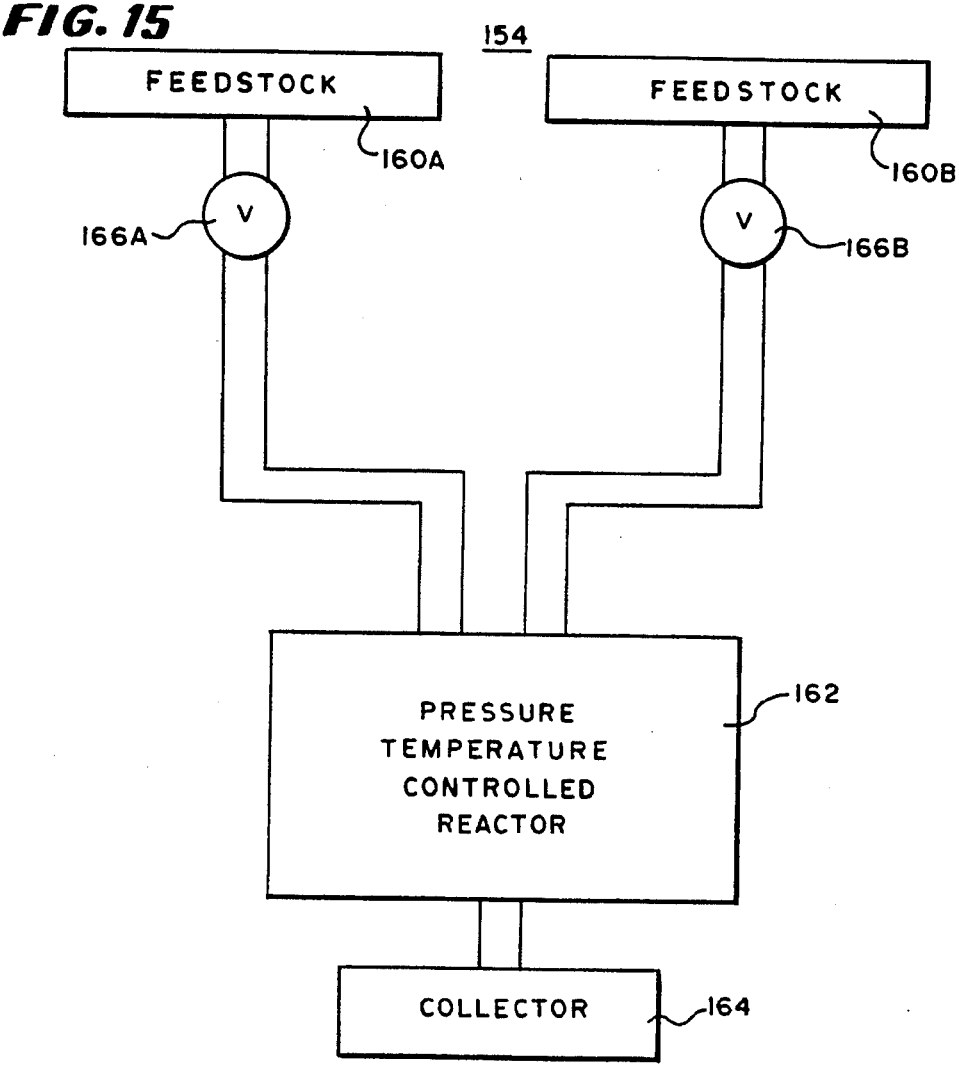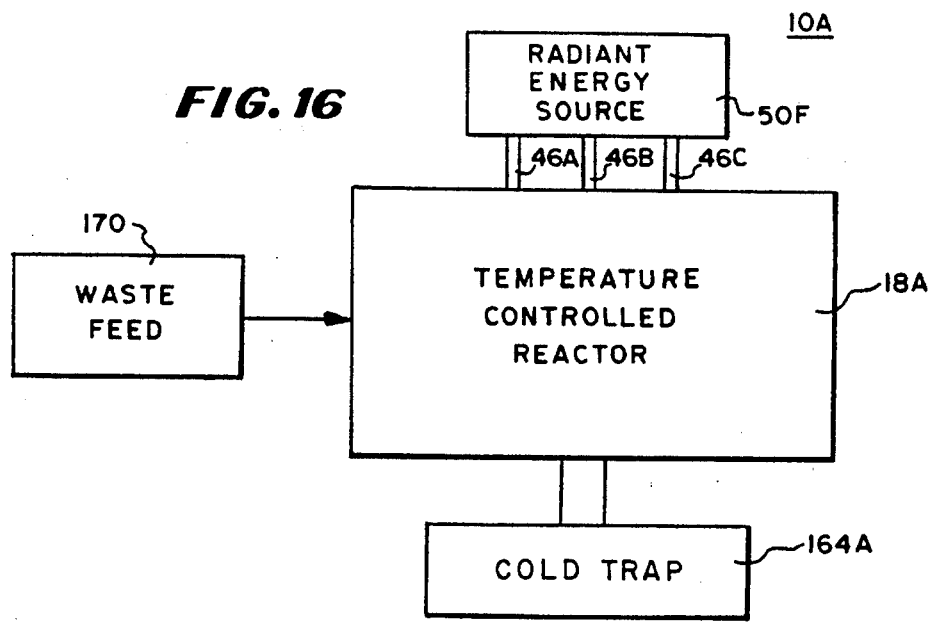

FORMING FINE PARTICLES

RIGHTS IN THE UNITED STATES GOVERNMENT

This invention was made with federal support under contracts DAAA15-85K-0001 and DAAL03-87-K0128 from the Department of Defense. The government has certain rights to the invention.

RELATED CASES

This application is a division of application Ser. No. 08/000,371, filed Jan. 4, 1993, now U.S. Pat. No. 5,390,864, and a continuation-in-part of application Ser. No. 07/712,724, filed Jun. 10, 1991, now U.S. Pat. No. 5,176,328, which is a division of application Ser. No. 07/492,928 filed Mar. 13, 1990, for FORMING FINE PARTICLES filed in the name of Dennis R. Alexander, now U.S. Pat. No. 5,044,565.

BACKGROUND OF THE INVENTION

This invention relates to apparatuses and techniques for forming and using fine particles.

It is known to fragment materials into small particles by vapor explosion. In vapor explosion, energy is applied to the interior of the material causing it to rapidly expand and form ultrafine particles in an explosion-like effect.

Early publications discussing vapor explosion are "Dynamics and Energetics of the Explosive Vaporization of Fog Droplets by a 10.6-UM Laser Pulse", by Peter Kafalas and Jan Harrman, *APPLIED OPTICS*, v. 12, n. 4, April 1973, pp. 772–775 and "Fog Droplet Vaporization and Fragmentation by a 10.6-UM Laser Pulse", by Peter Kafalas and A. P. Ferdinand, Jr., *APPLIED OPTICS*, v. 12, n. 1, January 1983, pp. 29–33. Moreover, U.S. Pat. No. 4,620,098 describes the formation of ultrafine particles of several useful compounds using lasers and gas dispersion.

There are several known practical uses of apparatuses and processes that generate particles. One such use is in spray painting and another is for nebulizers in medicine. In prior art spray painting equipment, the particles are formed by high velocity gases or vibrators. The use of high velocity gas flows has the disadvantage of wasting substantial amounts of paint as a result of the aerodynamic flow around objects and the use of vibrators, such as piezoelectric crystals, has a disadvantage in that the piezoelectric crystals which have commonly been used with the high velocity gas flows create particles larger than desirable for some applications.

SUMMARY OF THE INVENTION

Accordingly, it is an object of the invention to provide a novel method and apparatus for preparing and controlling fine particles in accordance with their use.

It is a further object of the invention to provide a novel method and apparatus for forming particles by vapor explosion and/or plasma formation and controlling the particles in accordance with a specific use of the particles.

It is a still further object of the invention to provide a novel method and apparatus for laser vapor explosion and/or plasma formation of materials to form fine particles and the use of fine particles resulting therefrom at low velocities.

It is a still further object of the invention to provide a novel technique for coating surfaces.

It is a still further purpose of the invention to provide a novel technique for forming and using sprays.

It is a still further object of the invention to provide a novel technique for forming and using irregularly shaped particles.

It is a still further object of the invention to provide a novel technique for causing physical and chemical processes to occur under high temperature and pressure in a continuous process.

It is a still further object of the invention to provide a novel technique for combustion.

It is a still further object of the invention to provide a novel fuel injection apparatus for motors.

It is a still further object of the invention to provide a novel nebulizer for application of medication.

It is a still further object of the invention to provide a novel injector for gas chromatographs.

It is a still further object of the invention to provide a novel technique for forming spray of materials that are degraded with heat.

In accordance with the above and further objects of the invention, a feedstock material is selected and converted to very fine particles by vapor explosion and/or plasma formation. The particles are collected to the appropriate density and are applied to the place they are to be used in a controlled flow, which is low velocity in most applications.

To cause vapor explosion and/or plasma formation, energy is introduced into the feedstock material by a laser beam. The particles are formed to be no more than 1 millimeter in diameter by controlling the energy, and after the particles are formed. Usually, they are moved by the flow control means at a velocity no greater than 5 meters per second. Generally, the pressures will be lower than 1 atmosphere above atmospheric pressure. For most applications, the particles will be less than 500 microns in diameter and the velocities lower than $\frac{1}{10}$ to $\frac{1}{2}$ meter per second. The described velocity is partly determined by the diameter of the exit port and should generally be low enough to avoid turbulence.

Preferably, one or more feeders supply the feedstock to one or more focused lasers which create the vapor explosion. In some applications, such as the coating of objects, vapor explosion and/or plasma formation will be within or near a mass controller. The mass controller in these applications confines the ultrafine particles and may accumulate particles from more than one source as appropriate. A flow controller moves the particles from the mass controller to the place where they are to be utilized such as by applying them to a surface as paint. In other applications, such as combustion, the fine particles may remain substantially in one place and are acted upon such as by mixing with air and burning.

The feeder may be a container having a outlet port, preferably with a valve that controls the flow rate. The flow may be by gravity or pressure through an adjustable opening communicating with the area for vapor explosion. In the area for vapor explosion and/or plasma formation, the atomizer for causing vapor explosion and/or plasma formation advantageously transmits laser light at the proper frequency and irradiance in accordance with the refractive index and the amount and velocity of feedstock material to cause vapor explosion and/or plasma formation.

To supply the laser light, the atomizing means for vapor explosion and/or plasma formation may include a plurality of lasers or one laser. Preferably, the laser light is collected and transmitted to the proper location by a light pipe or beam or other light conductor. The irradiance may be measured for easier control. For many applications, the frequency and the power applied to the laser are controllable in a manner known in the art.

To use the particles such as in painting, the flow rate of particles is selected in relation to the thickness of the coat and the area velocity of the nozzle with respect to the surface. The feedstock feed rate is related to: (1) the rate of application of the particles; (2) the loss of particles; and (3) the conversion to and loss of vapor. The number of feeders and the flow rate from each feeder are taken into account to determine the feed rate into the particle control means. The particle control means may be a tube and its size and outlet port are are adjusted for the number and flow rate of the individual feeders.

The irradiance of the lasers are set and energized so that light is applied by beam conductors to the area of vapor explosion and/or plasma formation, causing particles to flow into the tube. The tube is pointed at the location of application of the particles and gas from a tank serving as a flow control means is turned on to provide: (1) gas flow at a pressure sufficiently low to avoid back pressure moving the particles back into the explosion area; and (2) gas flow at a flow rate sufficiently low to avoid venturi effects that might pull liquid from the feeders too rapidly.

The selection of frequency and irradiance of the light from the laser in accordance with the refractive index of the material and its rate of flow control the size of the particles developed. The particle size may be caused to be uniform and of a predetermined size by causing vapor explosion and/or plasma formation to occur at a selected energy level that is uniform in the exploding feedstock. The uniformity of energy level controls the spatial heating and may occur over a large area at a uniform energy level or only at an energy node with the energy node being controlled to be at the irradiance level needed.

The location of energy nodes is determined by frequency, angle of incidence, and irradiance of the radiation or irradiance and the size and refractive index of the material irradiated and spatial mode and polarization of the illuminating beam. For example, a gaussian beam at an acute angle of incidence to a radius of a particle (off axis) energizes the outside or off axis area of a particle, whereas plane waves at any angle and gaussian waves on axis (radial to particle) focus energy at one or more small continuous volumes or nodes within the particle.

Instead of causing vapor explosion and/or plasma formation, the feedstock material may be caused to undergo chemical reactions or physical changes in a continuous process. To cause such reactions or physical changes, the feedstock is moved in a continuous column or stream or aerosol stream and impacted with light from the laser or lasers to create pressure and temperature: (1) below the vapor explosion and/or plasma formation level but high enough, such as several atmospheres of pressure, to cause the chemical reaction or physical reaction; or (2) to cause vapor explosion or plasma formation and photo assisted combustion. This pressure and temperature may be used to make chemical and physical changes in the feedstock material or burning in a continuous process.

From the above description, it can be understood that the method and apparatus of this invention has several advantages, such as: (1) extremely small particles may be formed without the use of high velocity gases or liquid pressure; (2) the particles may be easily controlled to be useful without excessive waste or undesirable conversion to aerosol at low irradiance, such as for painting or for the general formation of aerosols such as in medical applications or spraying insecticides or the like; (3) there is reduced waste of the feedstock material because of the low velocity and small amount of vapor formed; (4) contamination and air pollution are reduced; (5) instead of forming particles or along with particle formation, the pressure and temperature may be controlled to cause continuous on line physical and/or chemical reactions; (6) high temperature combustion or incineration capable of reducing a wide range of waste products to a more desirable form; and (7) providing more complete combustion of fuel through photon enhanced combustion processes by producing excited free radicals.

SUMMARY OF THE DRAWINGS

The above noted and other features of the invention will be better understood from the following detailed description, when considered with reference to the accompanying drawings, in which:

FIG. 15 is another embodiment of the invention utilizing parts substantially the same as the prior embodiments but providing an entirely different effect; and FIG. 16 is another embodiment of the invention as used for combustion or incineration.

DETAILED DESCRIPTION

Figure 1:
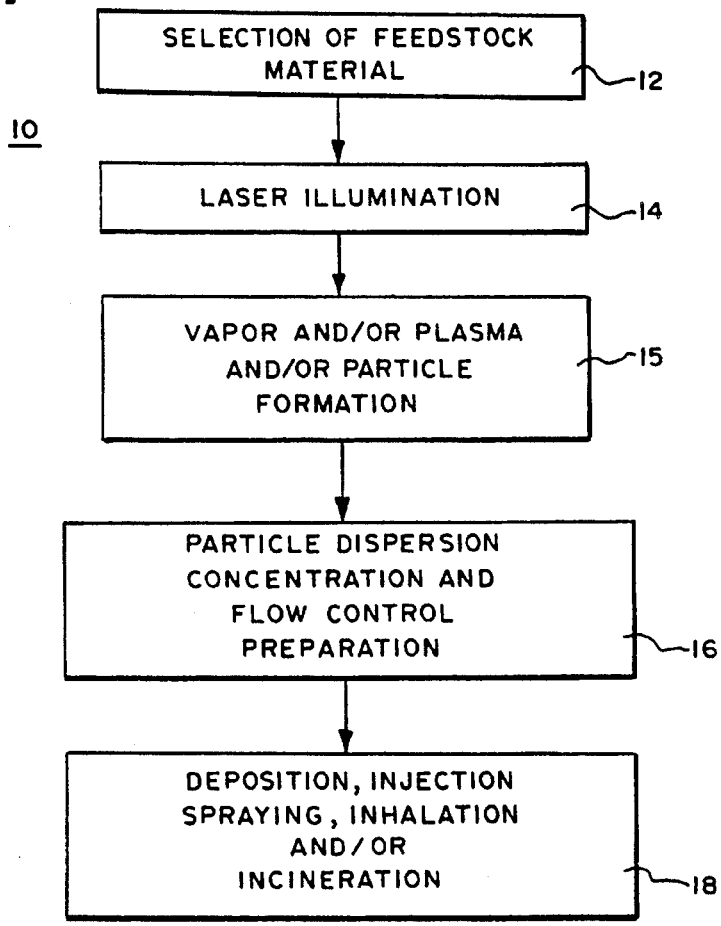
FIG. 1 is a block diagram of a process for forming and using small particles in accordance with the invention.

In FIG. 1, there is shown a block diagram of a process 10 for forming and using small particles including the step 12 of selection of feedstock material, the step 14 of laser illumination, the step 15 of particle, vapor and/or plasma formation, the step 16 of particle dispersion, concentration and flow control preparation and the step 18 of deposition, injection, inhalation, spraying and/or incineration. In this process, liquids such as paints or medical liquids which are to be broken into fine particles for application are illuminated with electromagnetic energy, usually a laser, to cause them to break into very fine particles. In some embodiments, after the selected feedstock reduced to small particles, the small particles are gathered together or dispersed to the proper concentration and then are caused to move to the location where particles are to be utilized as indicated by step 16.

The step 14 of laser illumination and the step 15 of vapor and/or plasma and/or particle formation utilize the energy from a laser. In the preferred embodiment, light from a laser is transmitted into the material at the appropriate frequency and irradiance for that explosion and/or plasma formation, thus resulting in a low velocity cloud or mist of fine particles. The particle dispersion, concentration and flow control preparation 16 may require the confinement of these particles, which confinement is possible because of their large drag coefficient in a confining gaseous environment and as a result, produce low velocity particles. The confinement need only be to the appropriate density at which they are to be moved at low velocity to the place of utilization as indicated by the flow control step 16.

In this specification, electromagnetic size transformation means particle formation, vapor explosion and/or plasma formation. In this specification, particle formation, vapor explosion and/or plasma formation means separating contiguous portions of feedstock material in the solid phase or liquid phase into vapor or particles or both, either charged as in a plasma or not charged. The particle formation means forms small particles without converting more than 20 percent of the material into the vapor phase. Small particles are particles having a diameter in the case of a sphere, or a largest dimension in the case of irregularly shaped particles, no greater than ½ of a millimeter (500 microns). If vapor is desired, this can be accomplished by increasing the power of the laser. The contiguous portions of feedstock material are separated into small particles by introducing electromagnetic energy into the feedstock material.

In this particle formation, vapor explosion and/or plasma formation process, the electromagnetic energy is generally introduced by a laser beam, the characteristics of which are selected to have power sufficient for the accumulation of the appropriate amount of energy in the material to be separated into particles by vapor explosion and/or plasma formation and to be at a frequency appropriate for this material.

The frequency of the applied electromagnetic energy, the refractive index of the material to be broken into particles and the power at which the electromagnetic energy is applied all affect the internal energy level within the feedstock material and are selected to cause the vapor explosion and/or plasma formation. This internal energy level may be expressed either in terms of an electromagnetic field irradiance or in terms of temperature. Generally, it is accepted that vapor explosion and/or plasma formation will occur at temperatures 9/10 of the critical temperature of the feedstock material. The localized heating effect from a laser beam of given irradiance is directly related to the refractive index of the material.

Critical temperature in this specification has its usual meaning which is the temperature of the liquid-vapor critical point which is also the temperature above which feedstock material has no liquid-vapor transition. Obviously, the introduced power is related to the associated energy needed for the vapor explosion and/or plasma formation and to the velocity between the laser beam introducing the power and the feed rate of the material which is being exploded.

Figure 2:
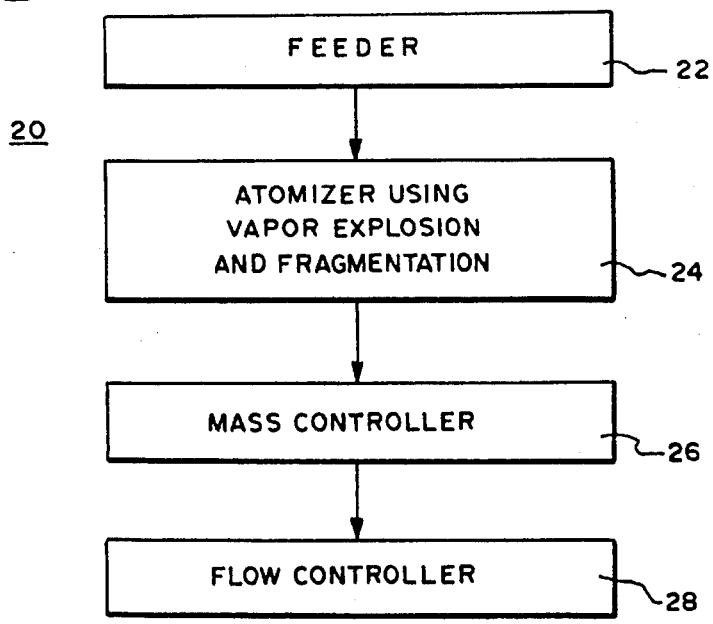
FIG. 2 is a block diagram of an apparatus for forming and using particles in accordance with the invention.

In FIG. 2, there is shown a block diagram of apparatus 20 for forming and using small particles having a feeder 22, an atomizer using vapor explosion and fragmentation 24, a mass controller 26 and a flow controller 28. The feeder 22 supplies a material to the atomizer 24 which breaks it into particles of less than 500 microns by vapor explosion and/or plasma formation and supplies them to a mass controller 26 which controls the density of the particles and the amount of mass. The flow controller 28 uses the particles in a process, such as for painting or forming medical sprays or the like.

To supply the feedstock material, the feeder 22 contains means for controlling the rate at which the feedstock material is supplied. As a simple example, it may be a container for a liquid having a small orifice at its bottom through which the liquid flows in a steady stream by gravity at a rate controlled by the size of the orifice. The liquid may be any liquid that is to be used as fine particles such as, for example, paint to be used in spray painting or fuel to be atomized in fuel injection.

The atomizer using vapor explosion and fragmentation 24 receives the feedstock material from the feeder 22 and applies energy to it as it flows from the feeder 22, breaking the material into particles of the desired shape. It supplies energy generally by laser at an irradiance and for a time sufficient to cause vapor explosion and/or plasma formation. Upon formation, the particles are substantially confined for later use.

The mass controller 26 works in conjunction with the flow controller to provide a confined working area from which the particles may be directed to the proper source. For example, it may be a simple compartment which is slightly pressurized to move the particles at a low mist velocity. In this specification, low mist velocity means that the average velocity of all of the particles in a single direction toward their ultimate destination is less than 1 meter per second and has a pressure exerted by the particles of less than 1/10 of an atmosphere above atmospheric pressure.

The feeder 22 may contain one or several sources of feedstock material either used in conjunction with each other or individually to supply several streams of fluid for atomizing, using vapor explosion and/or plasma formation. The particles formed by the vapor explosion and/or plasma formation may be accumulated in either a single mass controller 26 or a plurality of mass controllers. Several containers may be used to reach the proper density in the mass controller 26 for the particular application while maintaining the size of the material being moved within a range suitable for atomization by one or a plurality of laser beams.

In FIG. 3, there is shown a partly sectioned and partly schematic view of a feeder 22 and atomizing means 24A and 24B (24 in FIG. 2) using vapor explosion and/or plasma formation in which the feeder 22 is coupled to the atomizing means 24A and 24B in such a way that liquid within the feeder 22 flows at a controlled rate past a vapor explosion and/or plasma formation location or area to form fine particles and vapor for application to the mass controller 26 (not shown in FIG. 3) which confines the particles and vapor if vapor is to be used.

As shown in FIG. 3, the feeder 22 includes a housing 30, having a cavity 32 for containing a liquid, an outlet port 34, a valve 36 for controlling flow through the outlet port 34 and a coupling fixture 38 for coupling the atomized particles and vapor to the mass controller 26 (FIG. 2). The cavity 32 may contain any liquid from which it is desired to form particles, such as a paint which is to be used in a spray painting operation or medical liquids to be vaporized in a nebulizer for application to patients or fuel to be vaporized for combustion.

The outlet port 34 permits the liquid to flow under the force of gravity or under a slight pressure in a controlled stream through an explosion area 25 to form the particles, and the coupling fixture 38 is positioned to receive the particles while permitting them to be spread apart adequately to avoid their being combined into a liquid again. The valve 36 is positioned in the outlet port 34 to adjust the flow rate and can be any type of valve such as a needle valve or the like. The housing 30 may be pressurized or unpressurized for further control of flow rate as desired.

The atomizing means 24A and 24B for forming particles by vapor explosion and/or plasma formation include: (1) a plurality of transmission paths, three of which are partly shown at 40A, 40B and 40C; (2) one or more energy sources coupled to the transmission paths for application of energy, one of which is shown at 42C for the transmission path 40C; (3) a corresponding plurality of energy control portions, one for each energy source and transmission path, the energy controller 44C being shown coupled to the energy source 42C for explanation purposes; and (4) the explosion area 25.

While a plurality of transmission paths, energy sources and controls are contemplated in the preferred embodiment, only one is necessary if it provides adequate power and instead of being identical, different versions may be used to provide the proper combination of power for vapor explosion and/or plasma formation. For example, a femtosecond laser such as the type sold by Clark Instruments Inc. Box 500, 24 Chatham Woods, Pittsford, N.Y., 14354-0500, U.S.A. transmitting pules shorter than 100 femtoseconds in time duration at a high frequency may be used to increase the density of particles and produce even smaller particles in the nanometer size range or smaller. Frequencies in the range of 50 hertz to 10 kilohertz selected in such a way relative to the movement of the material being illuminated as to maximize the light used to form particles and minimize the light that is scattered or goes into heating the plasma. A plurality of lasers aimed from different angles can cause the field within the medium to be uniform, resulting in more uniform sized particles.

In the embodiment of FIG. 3, the light transmission paths such as 40A, 40B and 40C each include corresponding light conductors 46A, 46B and 46C which are coupled at one end to the energy sources such as the one illustrated by 42C in FIG. 3 and at the other end to corresponding lens arrangements 48A, 48B (not shown) and 48C for focusing light on the vapor explosion and/or plasma formation area.

The lens arrangements, such as 48A and 48C shown in FIG. 3, focus light channeled through the light conductors 46A–46C, light pipes or beam paths into the outlet port 34 at a vapor explosion and/or plasma formation area so that the energy may impinge upon the liquid flowing therethrough to create a fine mist of particles having a low velocity which move through the coupling fixture 38. With this arrangement, the liquid flowing through the cavity 32 is converted in a controlled amount to fine particles which are applied to the mass controller 26 (FIG. 2) for application to a surface by the flow controller 48 (FIG. 2).

To supply light to the transmission path 40C, the energy source 42C includes a lens-coupling assembly 50C, a laser array 52C and a meter 54C. The laser array 52C supplies light to the lens-coupling assembly 50C which collects an adequate amount of light for the energy required and applies it through the light transmission path 40C.

The collected light is measured by the meter 54C to properly adjust the power in accordance with the desired outlet particles using the energy controls 44C. Feedback controls may also be used between the meter 54C and the energy controls 44C where desired to control variations in the irradiance of light to provide predictable and reliable results. Similar energy sources are also provided for the other transmission paths.

The lens coupling assembly 50C includes a housing 60, a lens assembly 62 and a photocell 64. It is mounted to receive light from the laser array 52C and couple the light to the light transmission path 40C for transmission to the outlet port 34 from the feeder 22. The photocell 64 is coupled to the meter 54C by the conductor 80 to provide a signal thereto indicating the light irradiance.

The laser array 52C includes a plurality of lasers, three of which are shown at 70, 72 and 74 in FIG. 3. In the embodiment of FIG. 3, the lasers are diode lasers but may be any type of laser. The light output is varied by the number of lasers and the controls which apply power to the lasers. In some cases, the frequency may be tunable to accommodate different liquids with different refractive indexes and in other cases, they are fixed for a fixed purpose such as a fixed source of medication, or a fuel injection system using only a specific fuel or a particular painting operation along an assembly line so that its refractive index is not varied.

In FIG. 4, there is shown another embodiment of feeder 22C, partly sectioned and partly schematic, similar to the feeder 22 of FIG. 3 and having the same parts labeled with the same reference numbers. It is shown connected to the atomizing means 24A and 24B (24 in FIG. 2) in the same manner as the embodiment of FIG. 3. However, in the embodiment of FIG. 4, the feeder 22C includes rollers 39A and 39B which drive a solid such as an aluminum wire at a controlled rate. Thus, the valve used in the embodiment of FIG. 3 to control the flow rate of a liquid within the feeder is unnecessary.

In the embodiment of FIG. 4, the solid is advanced to or driven past the vapor explosion and/or plasma formation location or area to form fine particles and vapor for application to the mass controller 26 (not shown in FIG. 3) which confines the particles and vapor, if vapor is to be used, in the same manner as particles are formed from a liquid in the embodiment of FIG. 3.

In FIG. 5, there is shown a portion of an apparatus for forming and using small particles particularly useful in coating applications, such as painting, and having a feeder 22, a particle control means 26A, a flow control means 28A and a work piece such as 90 which is to be coated, such as by spraying. The work piece 90 may be adapted to be moved with respect to the apparatus for forming and using small particles such as on an assembly line in which the work piece 90 is one of a series of items, each of which are to be painted with the same color.

The feeder 22 shown in FIG. 5 includes a plurality of feeder units 22A and 22B each of which may share an energy source or may have its individual energy sources. One or any number of feeder units may be utilized, and in the embodiment of FIG. 5, two are utilized. The number of feeder units is selected to provide an appropriate density of particles in the particle control means 26A consistent with the required flow of particles for function of the apparatus and with the appropriate coordination of the laser energy and the stream of feedstock material that is being converted to particles.

Figure 5:
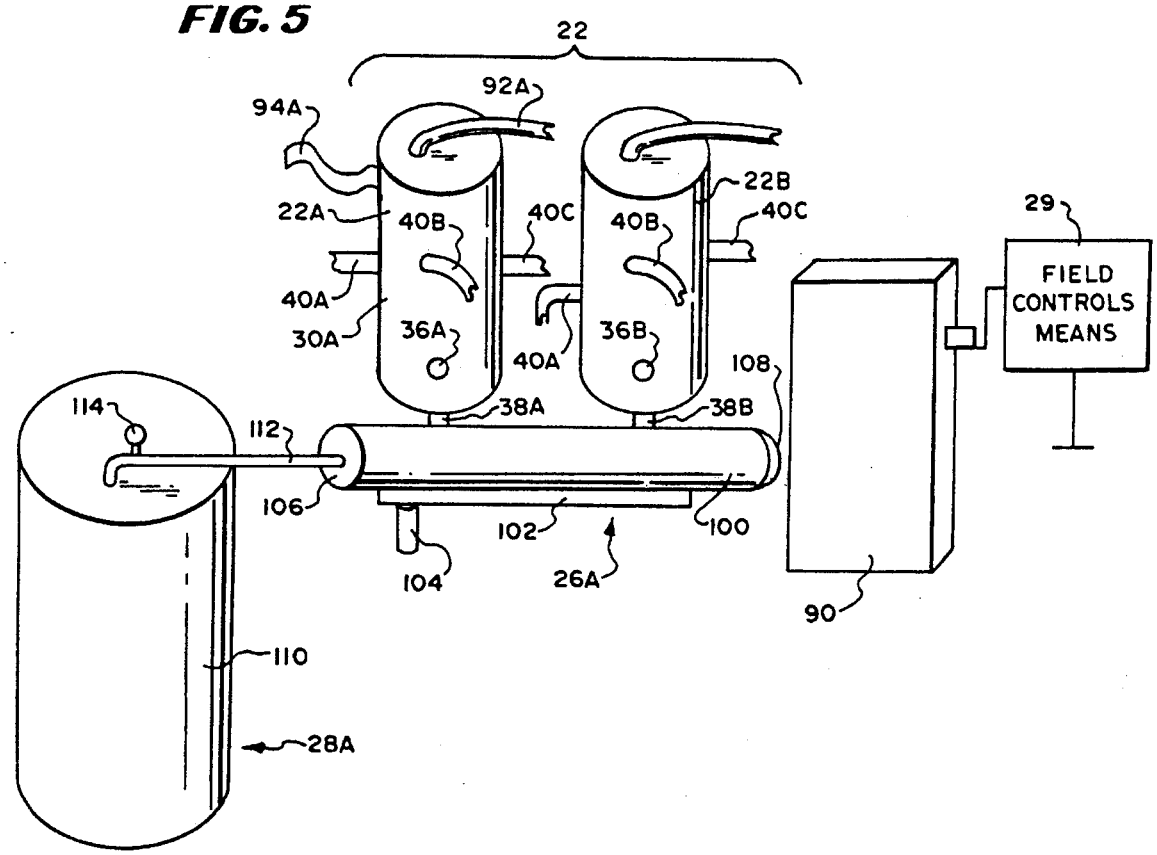
FIG. 5 is simplified perspective view of another portion of the apparatus for forming and using particles of FIG. 3 or FIG. 4.

In the embodiment of FIG. 5, the feeder units 22A and 22B are connected at spaced apart locations in a line along the particle control means 26A so that they feed particles in a series in line with pressurized gas supplied by the flow control means 28A. In this manner, the total flow rate of the particles to the surface to be painted or to receive an aerosol may be adjusted to a level greater than the maximum obtainable from one feeder.

The feeder units 22A and 22B are identical and only feeder unit 22A will be described herein. It includes a feeder housing 30A, a plurality of light conductors 40A–40C being shown in FIG. 5, a source of fluid (not shown in FIG. 5) for applying new fluid through a hose 92A, a source of pressure hose 94A and a control knob 36A for a valve to control the flow of particles formed in an explosion area (25 in FIG. 3) through a coupling unit 38A into the particle control means 26A.

The individual control valves 36A and 36B are generally adjusted to identical feed rates which together provide a sufficient number of particles from the particle control means 26A. The source of pressure through the hose 92A can also be adjusted to control the flow rate and new fluid may be applied through the source of pressure hose 94A to replace fluid that is being converted to particles and leaving the feeder housing 30A. For some applications, it is unnecessary to apply a pressure through the hose 92A and fresh fluid through the source of pressure hose 94A.

The number of feeders, the amount of particles to be produced by each feeder and the specific design of the feeders are all matters which are adjusted in accordance with the particular use of the apparatus. However, because the feeders are themselves adjustable and more than one feeder can be used, control of the rate of flow of particles from the particle control means 26A may be varied by the flow control means 28A over a wide range without exceeding the capacity of a single feeder.

The particle control means 26A in the embodiment of FIG. 5 is a tubular cylinder 100 having a recess 102 in its bottom wall with the lowest portion of said recess being stopped by a drain valve 104. Openings in the top of the tubular cylinder 100 provide a connection with the coupling units 38A and 38B to the feeder housings 30A and 30B to permit particles to flow into the particle control means 26A from the top. Cooling may alternatively be provided to the tubular cylinder 100 to cool and remove vapor through the drain valve 104. The drain valve 104 further serves to remove any excess flow of particles not broken into a fine mist. The flow control means 28A is connected to the tubular cylinder 100 at one end 106 and the outlet port 108 of the particle control means 26A may be aimed at the surface to be coated to move particles onto it.

The flow controller 28 (FIG. 2) in one embodiment 28A includes a pressurized tank of air communicating with the tubular cylinder 100 at the inlet 106 through a valved conduit 112, the flow and pressure from which is controlled by the valve 114. With this arrangement, low velocity air or other gas moves the particles against the surface to which they are applied. Since the particles have substantially no velocity within the particle control means 26A which confines them, very low velocity and low pressure air is adequate to move the particles, thus avoiding the escape of excessive vapor and an excessive number of particles.

In another embodiment used either with or separately from the embodiment 28A, the flow controller 26 includes a source of electric potential connected to the surface to be coated to draw charged particles toward the surface. The particles are charged by the vapor explosion and/or plasma formation, but in some applications a means for charging the particles other than the laser apparatus may be used.

Before using the apparatus for forming and using small particles, certain parameters must be determined, such as for example the mass flow rate of particles to accomplish each purpose, such as coating a surface. Under some circumstances, trial runs may be necessary.

The irradiance of energy applied to the stream of feedstock must also be known. In some cases, it can be calculated from a knowledge of the refractive index of the material and the flow rate. In other cases, it must be determined by a trial run and adjustments made to obtain the proper kind of particles.

The flow of pressurized air serving as a flow controller must also be either known or determined by adjustment to the valve 114. The pressure and flow rate must be adjusted so back pressure does not prevent the particles from leaving the adapter where they are formed and instead permits them to freely enter the particle control means 26A. Moreover, the flow rate must be sufficiently low so that venturi effects do not pull liquid downwardly before it can be properly atomized.

In operation, after the adjustments are made, the mass controller 26 is positioned, the lasers are energized, the feeder flow is adjusted and the feedstock material is applied in the proper manner such as for painting.

To adjust the lasers so as to provide the proper amount of particles at an appropriate rate, the operator selects the number of laser's in a laser array such as 50C, the type of lasers, the irradiance of their light, the frequency of the output if the lasers are tunable and the output of the power sources.

The power is adjusted with the power control means controlling the voltage and/or current to the lasers and the lasers are positioned so that light flows through the light pipes or beam paths into the area for vapor explosion and/or plasma formation. The flow rate is adjusted by the valves 36A and 36B and the number of feeders so that it flows into the tube 100 and the valve 114 is adjusted to the proper flow rate.

After the equipment is adjusted, the lasers are turned on so that particles are formed in the feeder by vapor explosion and/or plasma formation of liquid flowing downwardly, forming fine particles of the coating material. The flow through valve conduit 112 gently moves the particles at a velocity less than 5 meters per second against the work piece 90 to coat it.

During the coating, the outlet port 108 is positioned immediately adjacent to the work piece 90 pointing toward the location for deposition of the particles. If necessary, the drain Valve 104 is opened and in some embodiments, the tubular cylinder 100 may be water cooled, with liquid being collected from the drain valve 104 for recirculation or disposal to avoid pollution.

Although in the preferred embodiment, the particles are moved by gas pressure to the surface for coating or to any other location in which they are to be utilized, other conventional means of moving particles may be utilized. The particles are generally charged and may be electrostatically drawn to a surface. Moreover, additional charge may be applied to them. In some cases, it is possible to directly apply the particles or vapor to a surface directly from the vapor explosion and/or plasma formation process.

In forming the particles, uniformity of size of the particles is obtained by causing the vapor explosion and/or plasma formation to occur at the same energy level to have the same fluid mechanisms like thin film surfaces forming and breaking into filaments and then into droplets. This is done by creating a uniform field at certain points in a droplet which produce vapor explosion and/or plasma formation or 9/10 of the critical temperature or as a substitute for this, selecting the angle of incidence to a column or droplet or solid and frequency and irradiance which will create a node or multiple nodes of high energy for the vapor explosion and/or plasma formation. That node may occur at different locations but the vapor explosion and/or plasma formation creating the particles should create thin liquid films and/or ligaments without variations of more than 10 percent for uniformity and narrow size distributions. However, the higher and the shorter time of application of this irradiance at the time of the vapor explosion and/or plasma formation, the smaller the particles so that some control is exercised over the size of the particles.

Figure 3:
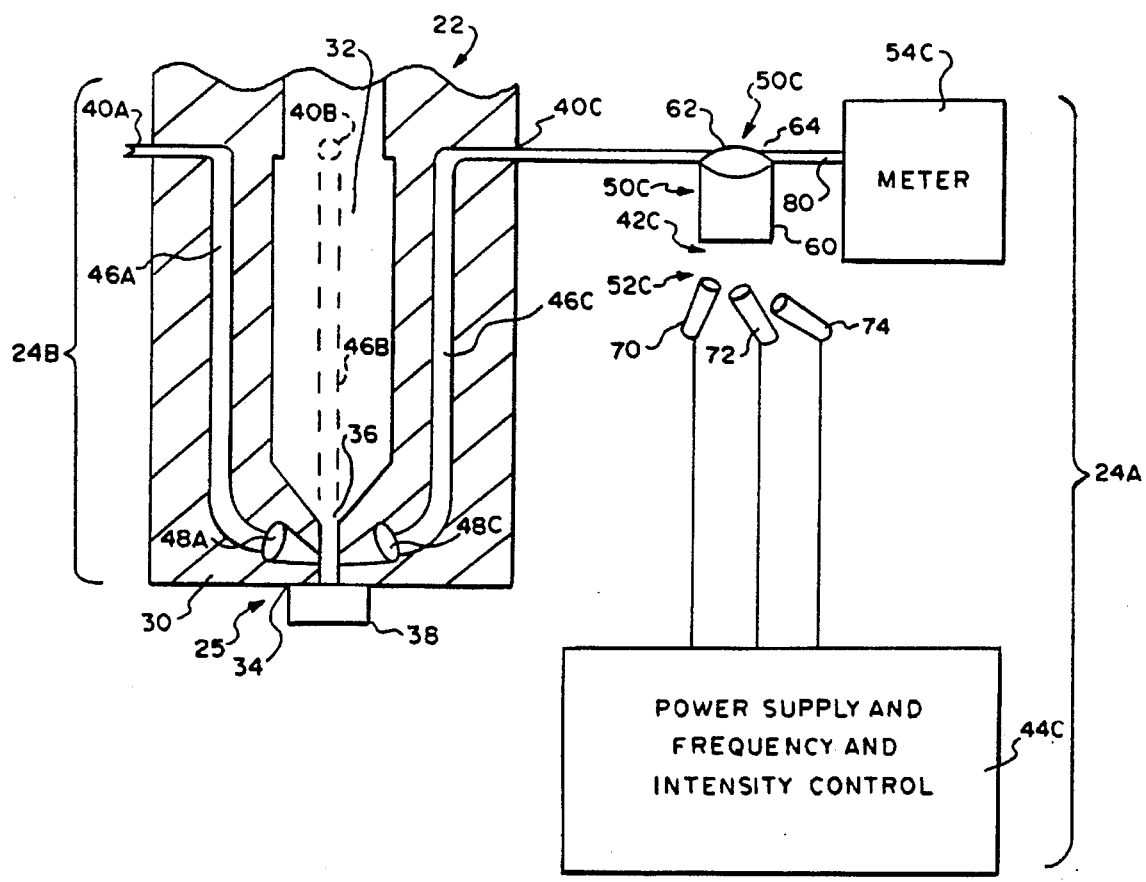
FIG. 3 is a partly schematic, partly sectioned, fragmentary view of a portion of the apparatus for forming and using particles in accordance with an embodiment of the invention.
Figure 6:
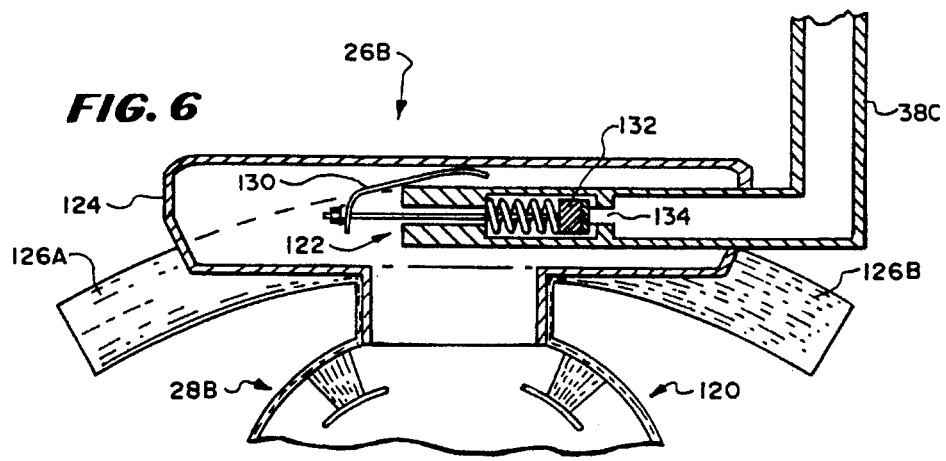
FIG. 6 is a simplified sectional view of a portion of the embodiment of FIG. 2 including a mass controller and a flow controller which are another embodiment of the invention.

In FIG. 6, there is shown another flow controller 28B and mass controller 26B, with the flow being controlled by inhaling action of a person through a mouthpiece 120 to draw particles from an atomizer using vapor explosion and/or plasma formation 34 of the type shown in FIG. 3 through tubing 38C into the patient. This mass controller 26B and flow controller 28B may be used with hospital nebulizers to draw saline solution particles and medication into the patient with efficiency.

In the embodiment shown in FIG. 6, the mass controller 26B includes a hollow housing 124, first and second exhaust tubes 126A and 126B communicating through check valves with the housing 124 to permit the expulsion of air under pressure but not permitting air to be drawn in, a valve assembly 122 communicating with the tube 38C to permit particles to be drawn in by vacuum pressure from the mouthpiece 120 but preventing exhaled air from the mouthpiece 120 from flowing into the tube 38C.

With this mechanism, a patient places the mouthpiece 120 in the patient's mouth. When the patient draws inwardly, particles are drawn through the tube 38C which may be elongated. The force of the inhalation bends the spring 130 in the valve assembly 122 pulling a valve element 132 away from a valve seat 134 to permit particles in air to enter it and flow there around into the mouthpiece 120. When the patient exhales, pressure causes the valve element 132 to fall against the valve seat 134 blocking the exhaled air from the tube 38C but permitting it to flow through the exhaust tubes 126A and 126B.

Figure 7:
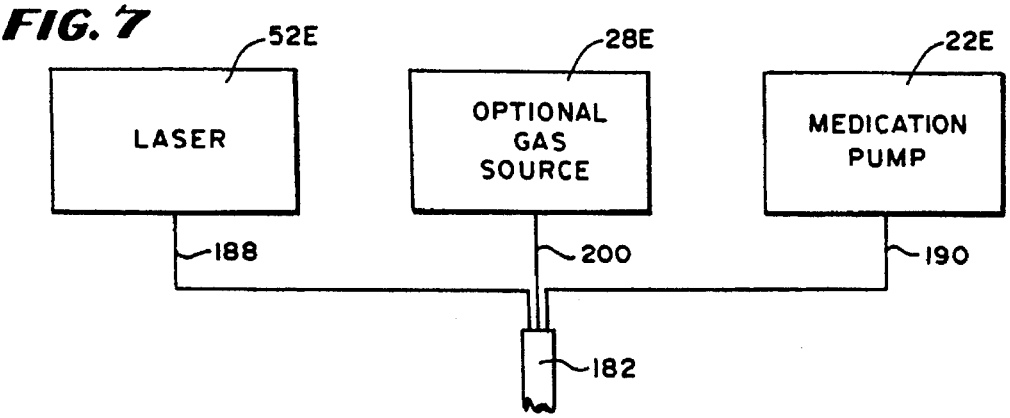
FIG. 7 is a fragmentary schematic view of another embodiment of the invention used for nebulizing medication.

In FIG. 7, there is shown a block diagram of another system for atomization and use of medical solutions for aerosol therapy including a laser or laser array 52E, a medication pump 22E, an optional source of gas pressure 28E, a delivery tube 182, a light conductor 188, a capillary tube 190 for the delivery of medication and a tube or conduit 200 through which a gas may be delivered if desired to help disperse atomized medication. The laser 52E transmits light through the light conductor 188 through the delivery tube 182 into a body cavity such as a lung, and there it meets with a source of medication which may come from a medication pump 22E delivered through the capillary tube 190. Near the location for the medication, the laser 52E is focused on the medication to atomize it, in which case it moves at a low velocity and pressure onto the tissue or may be dispersed more rapidly onto the tissue by slight gas pressure such as air or other gases compatible to the lungs. It is possible to atomize solids already positioned at the end of the tube 182 in some applications.

Figure 8:
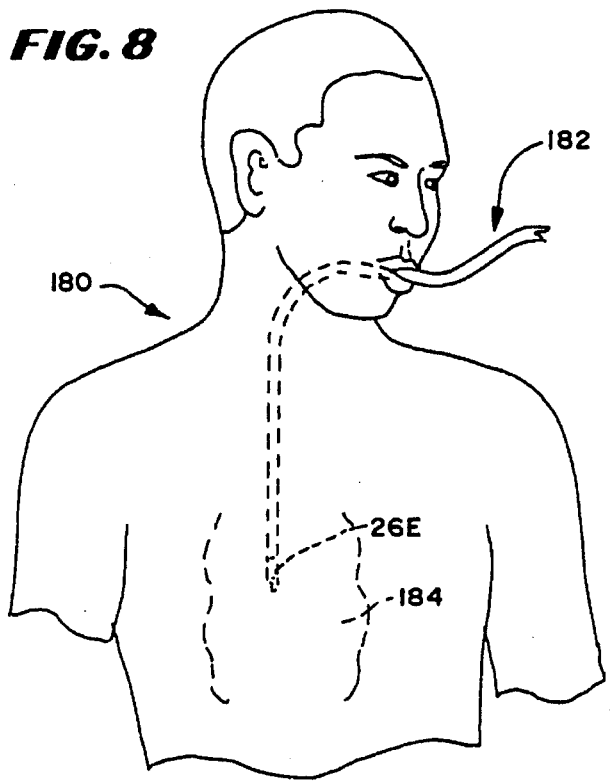
FIG. 8 is a fragmentary, simplified perspective view of the nebulizer of FIG. 7.

In FIG. 8, there is shown a schematic fragmentary view of a patient 180 receiving the tube 182 into a lung 184 where a mass controller 26E disperses the aerosol. The tube 182 may be of relatively narrow diameter and the laser 52E (FIG. 7) is focused in such a manner as not to endanger tissue but to atomize the material. The medication that condenses to form a liquid is absorbed by absorbent material in the tube 182 or caught in a cup-like portion of the sheath. Because the patient will normally be horizontal, an enlarged, open top portion is formed at a lower position near the exit end of the tube to collect liquid and the opening for the atomized medication is at an elevated position to disperse the atomized material while not permitting drops to escape into the lung.

The medication may be vaporized by a laser even though the medication is of a type that is prone to decomposition at high temperatures. The vapor explosion occurs without high temperatures being reached in a large portion of the medication and this lower temperature portion is atomized nonetheless, thus dispersing unaltered medication. For example, the bronchodilator, albuterol, and the protein, alpha-antitrypsin, have been tested, in vitro, using a neodymium-doped yttrium aluminum garnet laser and a carbon dioxide laser with satisfactory results.

Figure 9:
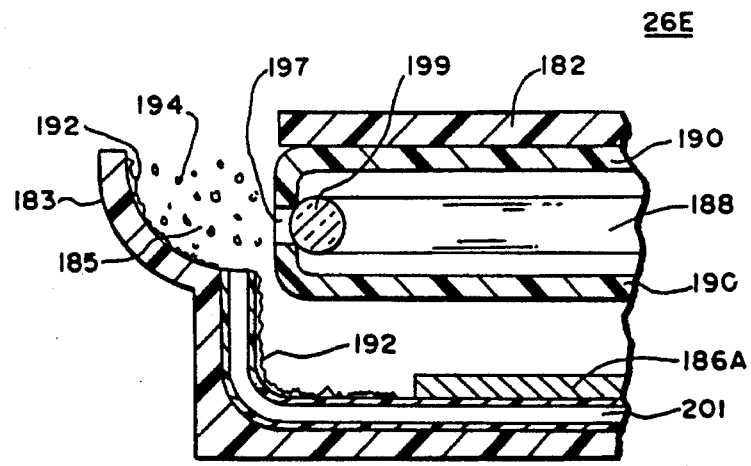
FIG. 9 is a fragmentary, partly-sectioned elevational view of a portion of the nebulizer of FIG. 7.

In FIG. 9, a mass controller 26E is shown in a partly broken-away and fragmentary sectional view. At the tip of the tube 182 are side by side markers 186A and 186B (186A being shown in FIG. 9, 186B being adjacent to and spaced from marker 186A) of a metallic material so that the position of the tube 182 can be determined by x-rays. It is desirable for the fine particles to be dispersed from the tube 182 while the exit 194 for the particles 185 is spaced slightly from the tissue and shielded while the tube 182 is horizontal. The proper position can be determined from the markers 186A and 186B using x-ray visualization to determine the approximate orientation and location of the exit end of the tube 182.

At the tip of the tube 182, there is an opening 194 which may open vertically and which has curved sides 183 so that it is elevated or opens upwardly to reduce the possibility of drops rather than uniform sized small fine particles being released. A liquid absorbing material 192, which may be any absorbent substance capable of absorbing fluids such as paper or plastic sponge substances, is positioned around the wall of the tube to absorb unatomized material.

Along the center of the tube 182, is the light conductor 188 and surrounding it coaxially is the medication tube 190 having an opening 197 of between 5 micrometers and 1 millimeter, preferably between 50 and 500 micrometers, and still more preferably 100 micrometers in diameter and terminating in an opening smaller than the tube in diameter than the laser 52E (FIG. 7) but within the range of 5 micrometers to 1 millimeter. The opening 197 opens into the particle opening 194 and the light conductor 188 and ball or focusing lens 199 terminates the light conductor 188 within the tube 190 just short of the opening 197.

With this arrangement, light from the light conductor 188 impinges upon the medication at an angle with respect to the wall of the curved sides 183 to avoid accidental impinging of the light against tissue. A gas dispersion capillary tube 201 may be provided to provide or pump gas, such as air, into the bottom of the opening 194 to aid in dispersing the medication.

Instead of the light conductor 188 and fluid tube 190 being coaxial, they may be side by side, with the fluid tube 190 bending over the end of the lens 199 to be atomized at the entrance to the opening 194.

Figure 10:
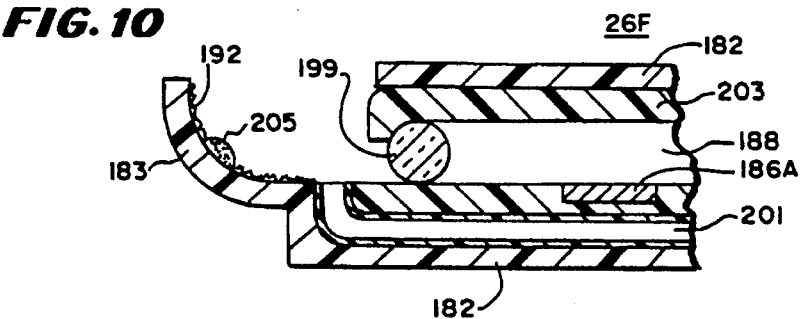
FIG. 10 is a fragmentary, partly-sectioned elevational view of another embodiment of the nebulizer of FIG. 7.

In FIG. 10, there is shown another embodiment 26F of a mass controller substantially the same as the embodiment of FIG. 9 and having correspondingly numbered parts. However, in this embodiment instead of a coaxially medication tube and a central light conductor, a sample of medication 205 in the opening 194 (FIG. 9) and a separate light conductor are used, spaced apart with the light focused on the sample by the lens 199 to atomize it. It operates in substantially the same manner, but with this configuration, solid sample may be supplied. The focus of the light conductor 188 is fixed by the inner supporting tube member 203. The tube 203 need not extend the full length of the tube 182 but must support the end portion of the light conductor 188 and lens 199 with respect to the sample 205.

Figure 11:
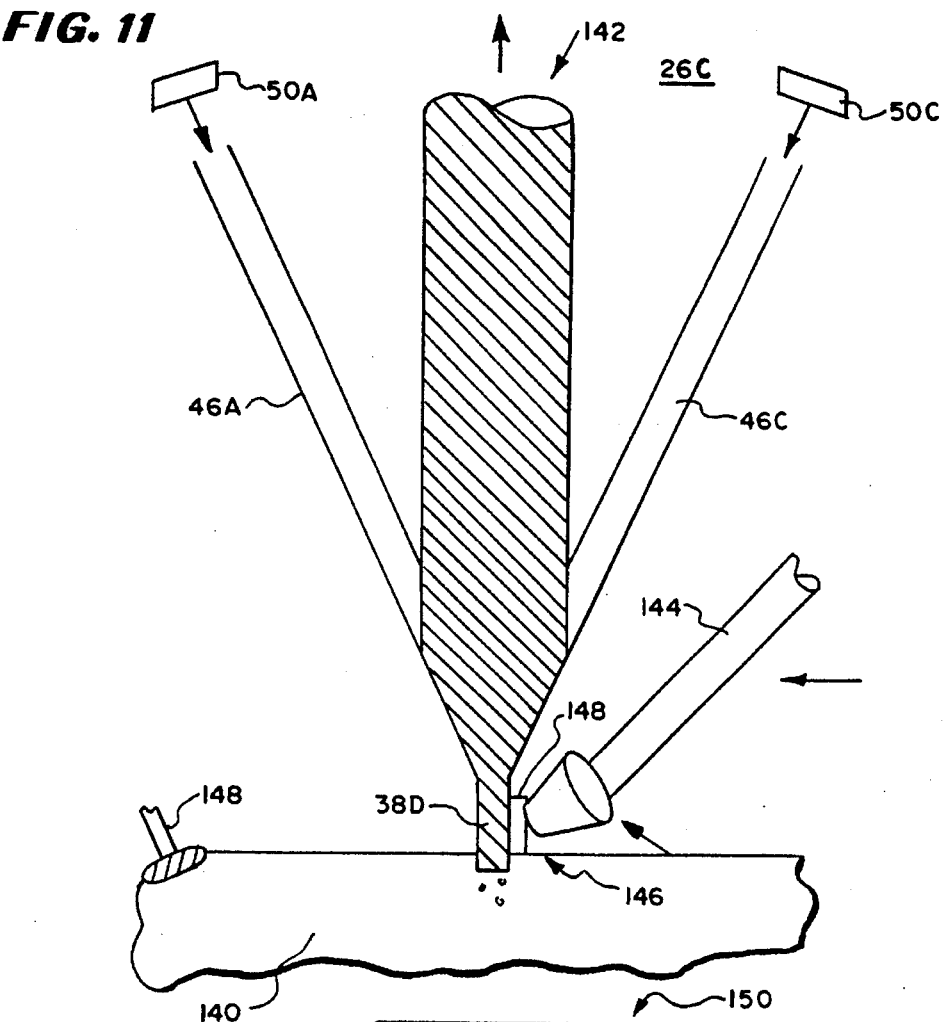
FIG. 11 is a simplified sectional view of a portion of another embodiment of the mass controller and the flow controller in accordance with the invention.

In FIG. 11, there is shown another embodiment of mass controller 26C which serves as a carburetor for receiving particles of fuel such as gasoline through a tube 38D from the atomizer 50A and 50C using vapor explosion and/or plasma formation through conduits 46A and 46C. A controlled amount of particles are supplied to a heat engine shown in fragmentary form at 140 for even combustion. In the carburetor 26C, particles are drawn through the tubing 38D from the mass controller into an induction tube 144. An air filter 142 is mounted to the top of the induction tube 144 in a conventional manner and a pivotable throttle valve 146 is mounted to be adjusted in position and thus control the velocity of air drawn through the air filter 142 through the induction tube 144 into the engine 140. With this arrangement, particles are drawn by the flow of air from the tube 38D for burning in the engine 140 in a manner known in the art.

With this arrangement, uniform fine particles are drawn into the engine 140 where they are quickly burned in a uniform hot flame so that there is very little exhaust of combustible fuel. Moreover, while the particles may be conventional gasoline, other types of particles such as from coal, coal slurries or the like, if sufficiently fine, may be used in some heat engines such as 140.

Figure 12:
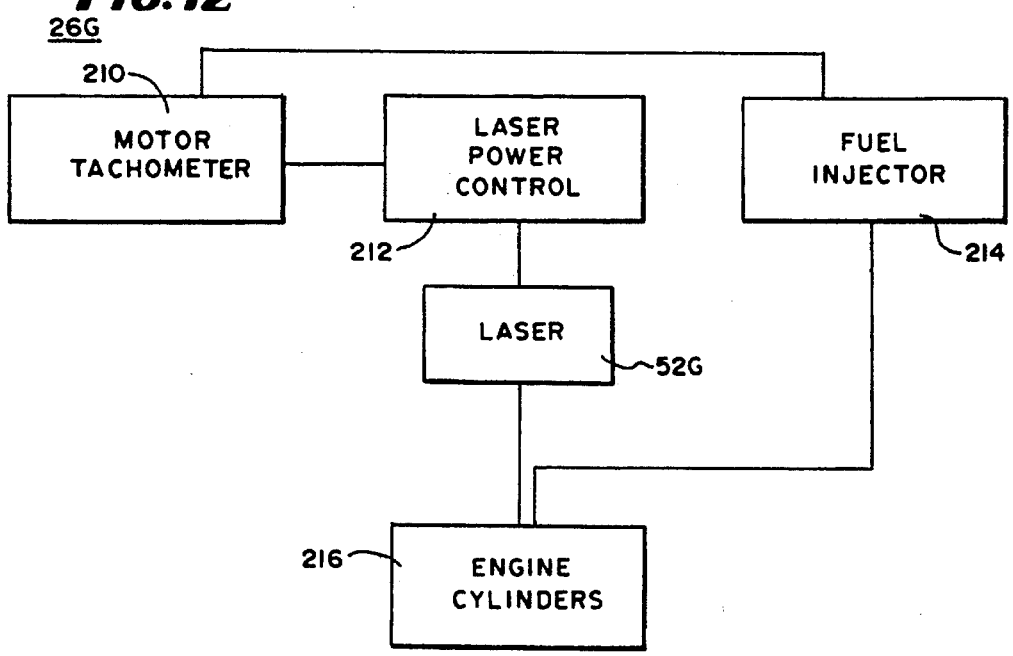
FIG. 12 is a block diagram of another embodiment of the invention which is a fuel injector for a diesel or gasoline engine.

In FIG. 12, there is shown a block diagram of another embodiment of fuel injection system 26G, not utilizing a carburetor, but otherwise being similar to the fuel injection system 26C. This system 26G includes a motor tachometer 210, a laser power control unit 212, a fuel injector 214, laser or laser array 52G and one or more engine cylinders 216. The motor tachometer 210 measures the speed of the pistons and causes the laser power control 212 to adjust the power of the laser 52G in accordance with the stroke of the piston to provide particles of different diameter depending on whether it is an in-take stroke or a compression stroke, the amount of compression and the mixture being used so as to provide optimum burning.

With this arrangement, the fuel injector 214 may also be controlled by the motor tachometer 210 to provide fuel to the end of a tube such as that shown in FIG. 11 for atomization to provide the proper amount of fuel and size of the particles. The power is adjusted partly in connection with the amount of fuel to obtain proper atomization and particle size and distribution of fuel in the amount demanded for that portion of the cycle.

Figure 13:
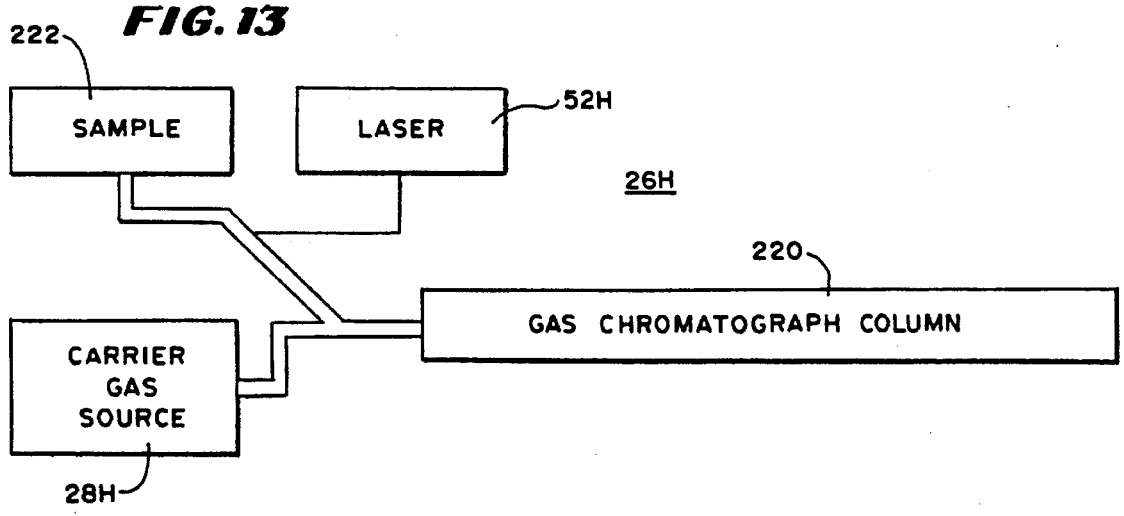
FIG. 13 is a schematic diagram of an injector for a gas chromatorgraph.

In FIG. 13, there is shown a system 26H for supplying sample to a gas chromatograph including a source of sample 222, a laser or laser array 52H, a carrier gas source 28H and a gas chromatographic column 220. With this arrangement, sample from the source 222 is supplied to an injector at a relatively low temperature where it is atomized by the laser 52H and carried into the gas chromatograph 220 by the carrier gas source 28H. Organic compounds such as the above mentioned albuterol and alpha-antitrypsin may be analyzed by a gas chromatograph 220 without heating the compounds to such temperatures as to decompose them. Many other compounds may be atomized by vapor explosion in the manner described above and made susceptible to gas chromatograph in a manner known in the art without such decomposition by vapor explosion.

Figure 14:
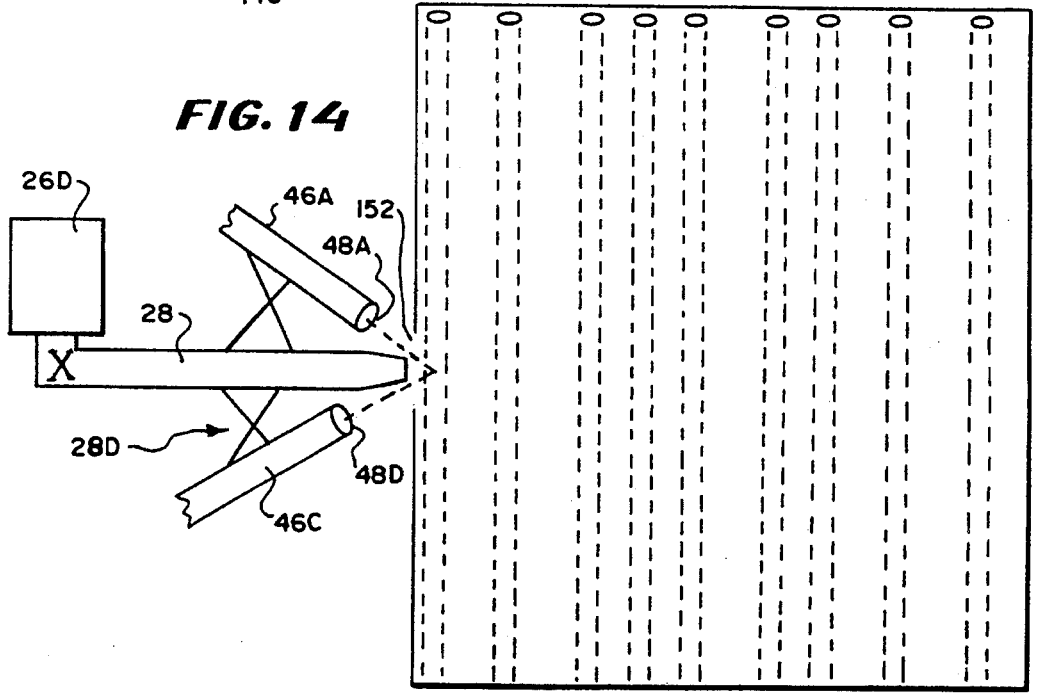
FIG. 14 is a simplified sectional view of still another embodiment of the mass controller and the flow controller in accordance with an embodiment of the invention.

In FIG. 14, there is shown a fragmentary view of a boiler having a mass controller 26D, a flow controller 28 and a plurality of boiler tubes 150 forming a portion of a boiler and a plurality of sources of radiation 46A and 46C. The air paths indicated generally at 28D control the feeding of the particles into the flame for burning. With this arrangement, the flow of fuel into the boiler is controlled, providing a higher degree of combustion and efficiency.

In each of these embodiments, particles are formed with a size dependent upon the irradiance. Localized irradiance is controlled by the refractive index of the material, the amplitude of energy applied to the material, the frequency of energy applied to the material, the length of the laser pulse applied to the starting shape of the material, and the angle of incidence to the material at which the electromagnetic energy is applied. The particle uniformity is controlled by the vapor explosion and/or plasma formation at a uniform localized irradiance.

In FIG. 15, there is shown a reactor 154 having first and second sources of feedstock 160A and 160B, a pressure and temperature controlled reactor 162 and a collector 164. The pressure and temperature controlled reactor 162: (1) communicates with the sources of feedstock 160A and 160B through valves 166A and 166B through which the flow of feedstock may be controlled; (2) creates pressure and temperature in the flow of feedstock in an on-line process for creating physical or chemical changes in one feedstock or more than one feedstock; and (3) communicates with the collector 164 which may be any suitable fraction collector or other collector for collection of the reaction product of the pressure and temperature controlled reactor 162.

While in FIG. 15, two sources of feedstocks 160A and 160B are shown controlled by valves 166A and 166B, obviously only one feedstock, such as plastic, is necessary in some applications and multiple feedstock sources may be used. In the case of some plastics, a single polyethylene or polyvinylchloride compound may, for example, be applied to the pressure and temperature controlled reactor 162 and through the proper exertion of pressure be made linear before being collected. Similarly, multiple sources of feedstock may be reacted together in the pressure and temperature controlled reactor 162.

Figure 4:
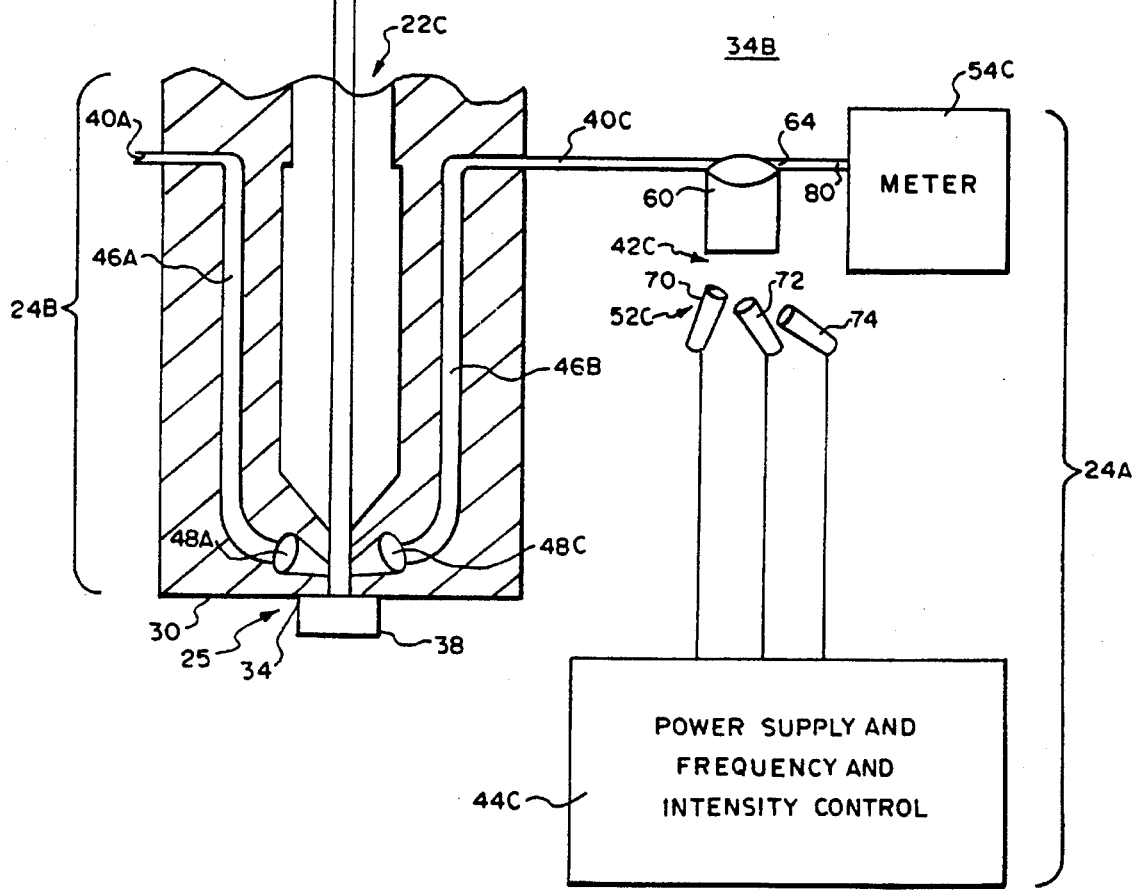
FIG. 4 is a partly schematic, partly sectioned, fragmentary view of another embodiment of the portion of the apparatus for forming and using particles similar to that of FIG. 3 but is intended to use a solid as a feedstock rather than a liquid.

The pressure and temperature controlled reactor 162 is substantially identical to the atomizer using vapor explosion and/or plasma formation 34, two embodiments of which are shown in FIGS. 3 and 4 indicated generally as 34A and 34B. However, the amplitude of the laser beams, frequencies and angle of incidence to the flow of fluid through the reaction section 34 are adjusted to be below 9/10 of the critical temperature at points in the column. With this adjustment, there is no vapor explosion and/or plasma formation but high temperatures and pressures are exerted in the column which cause the desired reaction depending on the selection of feedstocks. In this manner, chemical reactions requiring high temperatures and pressures may be utilized in a continuous process rather than in a batch process.

In FIG. 16, there is shown a laser incinerator apparatus 10A adapted to vaporize waste materials using vapor explosion and/or plasma formation and photon-aided burning having a source of laser energy 50F, a plurality of light conductors 46A, 46B and 46C, a temperature controlled reactor 18A, a waste feed 120 and a collector or cold trap 164A. The waste feed 120 pumps toxic liquids through a conduit or conveys solid material such as asbestos, glass and the like by other means such as an auger or conveyor into the temperature controlled reactor 18A where it is irradiated by extremely high energy lasers focused to produce high temperature plasmas sufficient to completely ionize and burn the waste materials. The plume from the incinerator may be condensed in cold traps 146A and the remaining gases filtered before release back into the environment. The waste material may be collected in a cold trap such as 164A (FIG. 16).

From the above description, it can be understood that the method and apparatus for forming and using fine particles of this invention has several advantages, such as: (1) extremely small particles may be formed without the particles having a large velocity or pressure; (2) the particles may be easily controlled to be useful without waste vapor or the like for painting or for forming aerosols or spraying insecticides or the like; (3) there is reduced waste of the feedstock material because of the low velocity and small amount of vapor formed; and (4) contamination and air pollution is reduced.

Although a preferred embodiment of the invention has been described with some particularity, many modifications and variations in the invention are possible within the light of the above teachings. Accordingly, it is to be understood that, within the scope of the appended claims, the invention may be practiced other than as specifically described.

What is claimed is:

1. A process for forming and applying small particles to a patient comprising the steps of:

selecting a feedstock material to be supplied to an interior part of the patient's body;

irradiating the feedstock material with radiant energy having a predetermined angle of incidence to the material at a predetermined point, having a predetermined wavelength and having sufficient intensity to cause the material to be formed into particles while in the patient's body; and guiding a direction of movement of the particles, whereby they may be applied to a particular part of the patient's body;

the step of forming fine particles including the step of vapor explosion and/or plasma formation of said material, whereby the particles are low velocity at least after moving a distance less than one inch from the predetermined point.

2. A process according to claim 1 in which the step of irradiating the feedstock material includes the step of preparing particles by directing a laser beam to the feedstock material with sufficient intensity to oblate the feedstock material into particles having a diameter of less than ½ millimeter and creating no more than 20 percent vapor and at least 80 percent particles.

3. A process according to claim 2 in which the step of directing the laser beam includes the step of directing a laser beam having a frequency, angle of incidence and wave length with respect to the surface of the feedstock material, the shape of the feedstock material and the refractive index of the feedstock material that causes at least one of a vapor explosion and plasma formation of relatively uniform particles.

4. A process in accordance with claim 3 in which the step of directing a laser beam to the feedstock material includes the step of directing a laser beam having an intensity, wavelength and angle of incidence with respect to the refractive index, shape and rate of movement of the feedstock material which results in a predetermined diameter of particles.

5. A process according to claim 1 in which the step of guiding the direction of movement of the particles includes the step of moving the particles with a velocity less than 1 meter per second and a pressure of less than 1.1 atmospheres.

6. A process in accordance with claim 1 further including a step of supplying the feedstock material; the step of supplying the feedstock material including the step of flowing the feedstock material into the patient's body through a tube and the step of irradiating including the step of irradiating the feedstock material with the light transmitted into the patient's body through a light conductor.

7. A process in accordance with claim 1 in which the step of guiding the direction of movement of the particles includes the steps of directing the particles to a location adjacent to a respiratory tract of a patient and permitting the particles to move into the patient.

8. A process for forming and applying small particles comprising the steps of:

selecting a feedstock material;

irradiating the feedstock material with radiant energy having a predetermined angle of incidence to the material at a predetermined point, having a predetermined wavelength and having sufficient intensity to cause the material to be formed into particles by at least one of vapor explosion and plasma formation; and directing the particles into a carburetor of an internal combustion engine, wherein the fine particles are moved into the carburetor at a low velocity at least after moving a distance less than one inch from the predetermined point.

9. A process for forming and applying small particles comprising the steps of:

selecting a feedstock material;

irradiating the feedstock material with radiant energy having a predetermined angle of incidence to the material at a predetermined point, having a predetermined wavelength and having sufficient intensity to cause the material to be formed into particles by at least one of vapor explosion and plasma formation; and directing the particles into a boiler; wherein the fine particles are moved into the boiler at low velocity at least after moving a distance less than one inch from the predetermined point.

10. A process for chemically changing material comprising the steps of:

selecting at least one feedstock material to be altered;

illuminating the at least one feedstock material with radiant energy having a predetermined angle of incidence to the feedstock material at a predetermined point, having a predetermined wavelength and having an intensity lower than that required for any one of vapor explosion and plasma formation but high enough to cause a chemical reaction in the feedstock material from pressures and temperatures created therein;

the pressure and temperature being at least 200 degrees Centigrade and two atmospheres respectively.

11. A method in accordance with claim 10 wherein at least two feedstock materials capable of chemically reacting together are selected and are illuminated together wherein a new material that is a reaction product of the two feedstock materials is formed.

12. A process for forming and supplying small particles to an engine comprising the steps of:

irradiating fuel with radiant energy having a predetermined angle of incidence to the fuel at a predetermined point, having a predetermined wavelength and having sufficient intensity to cause the fuel to be formed into particles; and controlling a direction of movement of the particles, wherein they are applied to a motor cylinder;

the step of forming fine particles including the step of at least one of vapor explosion and plasma formation.

13. A process according to claim 12 in which the step of irradiating fuel includes the step of directing a laser beam to the fuel with sufficient intensity to oblate the fuel into particles having a diameter of less than ½ millimeter and creating no more than 20 percent vapor and at least 80 percent particles.

14. A method according to claim 13 in which the step of directing a laser beam includes the step of directing a laser beam having a frequency, angle of incidence and wave length with respect to the surface of the feedstock material, the shape and the refractive index of the feedstock material that causes a vapor explosion and/or plasma formation of relatively uniform particles.

15. A method according to claim 12 further including the step of controlling the amount of fine particles applied to said motor cylinder in relation to the movement of a cylinder in the engine.

16. A process for forming and applying small particles to a gas chromatograph for analysis comprising the steps of:

selecting a sample material to be broken into particles;

irradiating the sample material with radiant energy having a predetermined angle of incidence to the sample material at a predetermined point, having a predetermined wavelength and having sufficient intensity to cause the sample material to be formed into particles;

injecting the particles into a gas chromatograph;

the step of irradiating the sample material including the step of vapor explosion and/or plasma formation of said sample material at the predetermined point.

17. A method according to claim 16 in which the step of irradiating the sample material includes the step of directing a laser beam to the sample material with sufficient intensity to oblate the sample material into particles having a diameter of less than ½ millimeter and creating no more than 20 percent vapor and at least 80 percent particles.

18. A method according to claim 16 in which the step of directing the laser beam includes the step of directing a laser beam having a frequency, angle of incidence and wave length with respect to the surface of the sample material, a shape and a refractive index of the sample material that causes at least one of a vapor explosion and plasma formation of relatively uniform particles.

19. A method in accordance with claim 16 in which the step of directing a laser beam to the sample material includes the step of directing a laser beam having an intensity, wavelength and angle of incidence with respect to the refractive index, shape and rate of movement of the sample material which results in a predetermined diameter of particles.

* * * * *